United States Patent [19]

Iwahara et al.

[11] Patent Number: 4,845,255

[45] Date of Patent: Jul. 4, 1989

[54] METHOD OF PREPARING CYCLIC DISILANYLENE-ACETYLENES

[75] Inventors: Takahisa Iwahara; Robert C. West, both of Madison, Wis.

[73] Assignee: Kanegafuchi Chemical Industry Co., Ltd., Japan

[21] Appl. No.: 227,703

[22] Filed: Aug. 3, 1988

[51] Int. Cl.$^4$ .................................................. C07F 7/08
[52] U.S. Cl. .................................................. 556/406
[58] Field of Search ...................................... 556/406

[56] References Cited

U.S. PATENT DOCUMENTS 2,607,791  8/1952  Goodwin ........................... 556/406
4,614,812  9/1986  Schilling ........................... 556/406

FOREIGN PATENT DOCUMENTS

152891(A)  9/1983  Japan ................................. 556/406
152892     9/1983  Japan ................................. 556/406
152893     9/1983  Japan ................................. 556/406

*Primary Examiner*—Paul F. Shaver
*Attorney, Agent, or Firm*—Welsh & Katz, Ltd.

[57] ABSTRACT

1,2-dichlorodisilanes are reacted with the diGrignard reagents of 1,2-diethynyldisilane to yield the eight-membered ring disilanylene acetylenes of the formula:

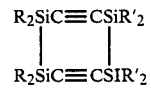

where R = an alkyl group, and R' = an alkyl group or an aromatic group.

14 Claims, No Drawings

METHOD OF PREPARING CYCLIC DISILANYLENE-ACETYLENES

BACKGROUND OF THE INVENTION

This invention relates to a method for preparing a cyclic ring structure and more particularly, to a method for preparing strained cyclic disilanylene-acetylenes.

Various types of organic, metal organic, and inorganic materials are known which have unusual highly anisotropic and potentially useful electric, optical, and/or magnetic properties. Such materials are known to be useful in fabricating electrical conducting materials, semi-conductors, electronic devices, and electromagnetic or acoustic sensors. The utility of some of these materials is frequently limited by such factors as weight, mechanical fragility, fabrication problems, corrosion, scarcity, and high costs.

Electronconductive organic materials have properties which can overcome or minimize such problems, and have the capability to be easily fabricated into films, filaments, and other shapes. Some of these materials are simply an organic compound containing a conductive material therein, such as a metal or graphite. Others comprise organic material whose electrical conductivities are established by chemical doping with electron acceptor and/or electron donor dopants. In general, the materials susceptible of establishing such electrical conductivity are characterized by highly delocalized $\pi$-electron conjugation, as may be found in most cyclic compounds or sometimes by $\sigma$-electron delocalization which may be found in polysilanes as well as the Si-C heterocyclic compounds. Electron delocalization between Si—Si $\sigma$ bonds and $\pi$ systems has been established for conjugated polysilyl compounds containing unsaturated or aromatic groups. Such $\sigma$-$\pi$ electron delocalization results in a strong ultraviolet absorption around 220-270 nm. Especially strong ultraviolet absorption at 250 nm has been found in the strained cyclic disilanylene-acetylene compound shown in Formula I.

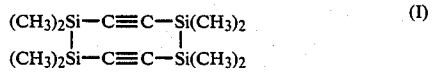

The compound of Formula I was obtained from the application of either heat or light to the nine-membered ring compound shown below.

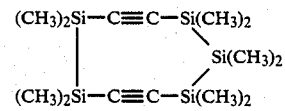

The compound of Formula I, because of its strong absorption in the near 250 nm wavelength, should have a high degree of $\sigma$-$\pi$ electron delocalization and therefore a high potential for use as an electroconductive material as well as an optical material. In addition, possibilities exist that the ring of the cyclic molecule might be opened and the cleaved molecule polymerized through the use of Na, K, or t-butoxide. Further, like polysilanes, the compound of formula I should undergo conversion to silicon carbide when heated to high temperatures.

SUMMARY OF THE INVENTION

Therefore an objective of the subject invention is a new method of preparing a cyclic silane compound with $\sigma$-$\pi$ electron conjugation.

A further object of the subject invention is a method of preparing a strained cyclic disilanylene-acetylene compound.

These and other objects of the subject invention are attained whereby a Grignard reagent is reacted with 1,2-diethynyldisilanes in a tetrahydrofuran solution to form a diGrignard reagent. The diGrignard reagent is reacted with a 1,2-dichlorodisilane in a dilute tetrahydrofuran solution. The strained eight-membered cyclic disilanylene-acetylene compound results, and can be isolated through conventional extraction techniques.

DETAILED DESCRIPTION OF THE INVENTION

The synthesis of a strained cyclic disilanylene-acetylene begins with the preparation of a diGrignard reagent. A diacetylene of the formula: HC≡C—SiR$_2$SiR$_2$—C≡CH (where R is an alkyl group, such as CH$_3$ or nC$_4$H$_9$) is reacted with a Grignard reagent, i.e., an alkylmagnesium halide, such as ethylmagnesium bromide, in a tetrahydrofuran (THF) solution. Other Grignard reagents such as methylmagnesium bromide, methylmagnesium iodide, n-propylmagnesium chloride, n-butylmagnesium chloride, sec-butylmagnesium chloride, and t-butylmagnesium chloride may also be used. The resulting diGrignard reagent is then reacted with a dilute THF solution of 1,2-dichlorodisilane of the formula ClSiR'$_2$SiR'$_2$Cl (where R' is an alkyl group such as CH$_3$ or nC$_4$H$_9$ or an aromatic group such as phenyl or p-tolyl) where it may be either refluxed or let sit 1-24 hours to yield the eight-membered ring disilanylene-acetylenes as follows:

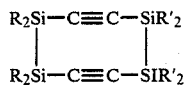

In general, tetrahydrofuran is used as a solvent in each of the reactions in the method of the subject invention. However, other ethereal solvents, such as diethylether, di-n-butylether, dimethoxyethane, dioxanes, etc. may also be used, as known in the art. It is important that the concentration of the solution be dilute (about 0.1M or lower) to avoid the possibility of a chain extending polymerization reaction dominating. Polymerization is observed even in dilute solutions, but if the diGrignard reagent in dilute solution is added at the same time the dichlorodisilane is added to the solvent, the cyclization reaction should dominate.

EXAMPLE 1

1.0 g (3.0 mmol) of HC≡C—Si(nC$_4$H$_9$)$_2$Si(nC$_4$H$_9$)$_2$—C≡CH and 3.0 ml (6.0 mmol) of 2M (mol/l) ethylmagnesium bromide in THF solution were mixed in 30 ml of THF to form 3.0 mmol of BrMgC≡C—Si(nC$_4$H$_9$)$_2$Si(nC$_4$H$_9$)$_2$—C≡CMgBr. To this was added 1.07 g (3.0 mmol) of ClSi(nC$_4$H$_9$)$_2$Si(nC$_4$H$_9$)$_2$Cl in 3 ml of THF. A mild exothermic reaction was observed. The solution was refluxed for four hours and the THF was pumped off. To the residue was added 30 ml of hexane and then 10 ml of aqueous NH$_4$Cl solution. The organic layer was separated out and the aqueous layer was extracted with 10 ml of hexane. The combined organic layer was washed with 30 ml of aqueous NH$_4$Cl solution three times, dried over CaCl$_2$, and evaporated to leave a viscous yellow liquid. A fractional kugelrohr distillation at a bath temperature of 205°–210° C., at 0.45 torr gave 1.36 grams (74% yield) of a clear viscous liquid, which was identified as the following:

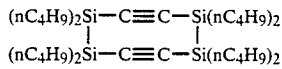 (II)

EXAMPLE 2

The procedure of Example 1 was used in making a diGrignard reagent from HC≡C—Si(CH$_3$)$_2$Si(CH$_3$)$_2$—C≡CH. This diGrignard reagent was then reacted with ClSi(CH$_3$)$_2$Si(CH$_3$)$_2$Cl as in Example 1. After the exothermic reaction, the solution was refluxed for four hours and the THF pumped off. Hexane and aqueous NH$_4$Cl was added to the residue, the organic layer was separated, and the aqueous layer was extracted with hexane, and the combined organic layer was washed with aqueous ammonium chloride solution three times, dried over calcium, chloride and evaporated. Sublimation at 70° C., 0.15 torr gave colorless crystals with a melting point of 138°–140° C. and having the structure of compound I.

EXAMPLE 3

The procedure of Example 1 was again followed, making a diGrignard reagent of HC≡CSi(CH$_3$)$_2$Si(CH$_3$)$_2$—C≡CH. The resulting diGrignard reagent was then reacted with ClSi(nC$_4$H$_9$)$_2$Si(nC$_4$H$_9$)$_2$Cl. After refluxing and extracting as in Example 1, kugelrohr distillation of the residue at 144°–150° C. yielded a viscous liquid determined to have the structure:

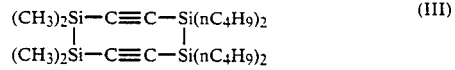 (III)

EXAMPLE 4

The procedure of Example 1 was used in making a diGrignard reagent from HC≡C—Si(CH$_3$)$_2$Si(CH$_3$)$_2$—C≡CH. This diGrignard reagent was then reacted with ClSiPh(CH$_3$)SiPh(CH$_3$)Cl as in Example 1 (Ph=phenyl group). After refluxing and extracting as in Example 1, kugelrohr distillation of the residue at 150°–180° C., 0.18 torr gave a clear viscous liquid, which was solidified to crystals later. The crude crystals were purified by recrystallization from EtOH twice to give colorless crystals with a melting point of 98°–99° C. and having the structure of compound IV:

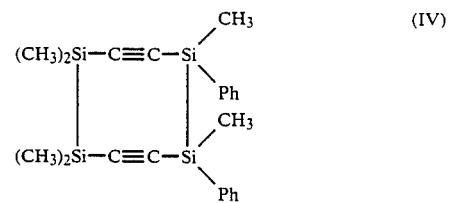 (IV)

Spectroscopic data for the above compounds are set forth in Table I. All of these compounds show ultraviolet absorption bands near 250 nm, which may be associated with the σ-π conjugation.

TABLE I

| | Properties of Cyclic Disilanylene-Diacetylenes | | | |
|---|---|---|---|---|
| Compound | Yield(%) | $^1$H NMR$^a$ | $^{13}$C NMR | $^{29}$Si NMR | UV(nm)$^b$ |
| I$^c$ | 67 | 0.25(s,24H) | −3.07$^{a.d.}$<br>119.46 | −33.62$^{a.d.}$ | 213<br>240(sh)<br>249 |
| II$^e$ | 73 | 0.59–0.81(brt,8H)<br>0.81–1.00(t,12H)<br>1.17–1.50(m,16H) | 13.04$^f$<br>13.09<br>26.83<br>27.69<br>120.22 | −27.04$^f$ | 215<br>240(sh)<br>250 |
| III$^g$ | 62 | 0.24(s,12H)<br>0.61–0.79(brt,4H)<br>0.79–0.96(t,6H)<br>1.20–1.50(m,8H) | −3.07$^a$<br>12.56<br>13.72<br>26.45<br>27.15<br>118.81<br>120.93 | −27.43$^a$<br>−33.07 | 215<br>250 |
| IV$^h$ | 45 | 0.28(s,6H)$^i$<br>0.34(s,12H)<br>7.34–7.47(m,6H)<br>7.55–7.68(m,4H) | | | 210<br>252 |

$^a$In CDCl$_3$.
$^b$In n-hexane.
$^c$Exact mass calcd for C$_{12}$H$_{24}$Si$_4$ 280.0955, measd. 280.0953.
$^d$Values in J. Am. Chem. Soc., 105, 3359 (1983).
$^e$Elemental Anal. Calcd for C$_{36}$H$_{72}$Si$_4$: C, 70.04; H, 11.76. Found: C, 69.87; H, 11.80.
$^f$In C$_6$D$_6$.
$^g$Exact mass calcd for C$_{24}$H$_{48}$Si$_4$ 448.2833, measd. 448.2841.
$^h$Exact mass calcd for C$_{22}$H$_{28}$Si$_4$ 404.1268, measd. 404.1259.
$^i$In CD$_2$Cl$_2$ In preparing the above compounds for the exhibition of electroconductive properties, the process commonly referred to as doping was utilized. A wide variety of doping materials may suitably be employed to attain electrical conductivity of the compound. Doping materials suitable for effecting an increase in the electrical conductivity of the strained cyclic disilanylene-acetylene compound of the subject invention are generally electron acceptor dopants, including for example I$_2$, $Br_2$, ICl, IBr, $SbF_5$, $AsF_5$, $Cl_2$, HBr, $BF_3$, $BCl_3$, $SO_2$, $SO_3$, $Cl_2$, $NO_2$, HCN, ICN, $O_2$, $SiF_4$, NO, $C_2H_2$, and transition metal carbonates, phosphine, and olefin derivatives.

In doping, the compounds are prepared by the method of the subject invention. The compounds are contacted with the dopant, which may take place in the gaseous or vapor phase, in solution. In any case, doping is by uptake of the dopant molecules into the disilanylene-acetylene molecule, which occurs pursuant to a degree proportional to the dopant concentration and the contacting period. For example, the cyclic disilanylene-acetylene compounds, in solid form, may be contacted by the gas $AsF_5$ under a pressure of 10 torr or by placing in a melt of $SbF_5$ for a contacting period ranging from a few minutes to over 24 hours to provide the desired degree of doping as known in the art. The doped substance may thereby be provided with a room temperature electroconductivity within the range of from about $10^{-1}$ to $10^{-10}$ $ohm^{-1}$ $cm^{-1}$ as measured using conventional techniques.

The doping procedure may also be carried out by placing the disilanylene-acetylene material in a solution of the dopant in an appropriate organic solvent inert to the disilanylene-acetylene, such as for example THF, n-hexane, or toluene. By trial and error, the length of time necessary to leave the disilanylene-acetylene in the solution is found which will obtain the desired degree of doping. At the completion of the doping, the doped material is removed from the solution and rinsed in an additional amount of the organic solvent to remove any residual doping solution therefrom. The excess solvent is pumped off by a vacuum and the conductivity of the disilanylene-acetylene is measured as known in the art.

Each of compounds I, III, and IV are separately heated to 1100° C. under an argon atmosphere and are thereby transformed to SiC.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments and equivalents falling within the scope of the appended claims.

We claim:

1. A method of preparing a cyclic disilanylene-acetylene comprising the steps of:
   (a) forming a diGrignard reagent by reacting a 1,2-diethynyldisilane with a Grignard reagent;
   (b) adding a 1,2-dichlorodisilane and allowing the reaction to occur; and
   (c) isolating the resulting cyclic disilanylene-acetylene compound of the formula

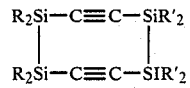

where R is an alkyl group and R' is an alkyl group or an aromatic group.

2. The method of claim 1 wherein said diethynyldisilane is of the formula: $HC\equiv C-SiR_2SiR_2-C\equiv CH$.

3. The method of claim 2 wherein R is selected from the group consisting of $CH_3$ and $nC_4H_9$.

4. The method of claim 1 wherein said Grignard reagent is selected from the group $C_2H_5MgBr$, $CH_3MgBr$, $CH_3MgI$, and $n-C_3H_7MgCl$.

5. The method of claim 1 wherein said 1,2-dichlorodisilane is of the formula: $ClSiR'_2SiR'_2Cl$.

6. The method of claim 5 wherein R' is selected from the group consisting of $(CH_3)$, $(nC_4H_9)$, and a phenyl group.

7. The method of claim 1 wherein R and R' are each selected from the group consisting of $CH_3$ and $nC_4H_9$.

8. The method of preparing a cyclic disilanylene-acetylene comprising the steps of:
   (a) forming a diGrignard reagent by reacting a 1,2-diethynyldisilane of the formula $HC\equiv C-SiR_2-SiR_2-C\equiv CH$ with a Grignard reagent;
   (b) adding a dichlorodisilane of the formula: $ClSiR'_2SiR'_2Cl$; and
   (c) isolating from the reaction mixture by solvent extraction a cyclic disilanylene-acetylene of the formula:

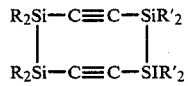

where R is an alkyl group and R' is an alkyl group or an aromatic group.

9. The method of claim 8 wherein R is selected from the group consisting of $CH_3$ and $nC_4H_9$.

10. The method of claim 8 wherein R' is selected from the group consisting of $CH_3$, $nC_4H_9$, and a phenyl group.

11. The method of claim 8 wherein said Grignard reagent is $C_2H_5MgBr$, $CH_3MgBr$, $CH_3MgI$.

12. The method of claim 8 wherein each reaction takes place in a solution of tetrahydrofuran.

13. The method of claim 12 wherein the reaction of diGrignard reagent with 1,2-dichlorosilane takes place in a dilute solution of tetrahydrofuran.

14. The method of claim 8 wherein said solvent is selected from the group consisting of tetrahydrofuran, diethylether, di-n-butylether, dimethoxyethane, and dioxanes.

* * * * *